(12) United States Patent
Robertson et al.

(10) Patent No.: US 8,557,783 B2
(45) Date of Patent: Oct. 15, 2013

(54) PHOSPHOTETRAHYDROPYRAN COMPOUNDS FOR THE TREATMENT OF WOUNDS AND FIBROTIC DISORDERS

(75) Inventors: Alan D. Robertson, Frenchs Forest (AU); Diego Silva, Frenchs Forest (AU); Ian Alexander McDonald, Frenchs Forest (AU)

(73) Assignee: Pharmaxis Pty Limited, Frenchs Forest (AU)

( * ) Notice: Subject to any disclaimer, the term of this patent is extended or adjusted under 35 U.S.C. 154(b) by 0 days.

(21) Appl. No.: 13/318,065

(22) PCT Filed: Apr. 28, 2010

(86) PCT No.: PCT/IB2010/000960
§ 371 (c)(1),
(2), (4) Date: Oct. 28, 2011

(87) PCT Pub. No.: WO2010/125445
PCT Pub. Date: Nov. 4, 2010

(65) Prior Publication Data
US 2012/0045455 A1    Feb. 23, 2012

Related U.S. Application Data

(60) Provisional application No. 61/173,416, filed on Apr. 28, 2009.

(51) Int. Cl.
*A61K 31/70*    (2006.01)
*A61K 31/7028*    (2006.01)

(52) U.S. Cl.
USPC ................................. 514/25; 514/27; 536/4.1

(58) Field of Classification Search
USPC ........................................ 514/25, 27; 536/4.1
See application file for complete search history.

(56) References Cited

FOREIGN PATENT DOCUMENTS

| WO | WO-02/04472 A1 | 1/2002 |
| WO | WO-2004/104015 A2 | 12/2004 |
| WO | WO-2009/138600 A2 | 11/2009 |
| WO | WO-2009/138601 A2 | 11/2009 |

OTHER PUBLICATIONS

Supplementary European Search Report dated Nov. 12, 2012.
Khanjin et al: "Synthesis of mannose-6-phosphate analogs: large-scale preparation of isoteric mannose-6-phosphnate via cyclic sulfate precursor" Tetrahedron Letters, vol. 43, No. 22, May 27, 2002 pp. 4017-4020.
Barragen et al: A mannose-6-phosphonate-cholesterylamine conjugate as a specific molecular adhesive linking cancer cells with vesicles Chemical Communications, Chemical Society London, Jan. 1, 2001, pp. 85-86.
Baudy et al., "Prodrugs of Perzinfotel with Improved Oral Bioavailability," J. Med. Chem., 2009, vol. 52, pp. 771-778.
Moeller et al., "The bleomycin animal model: A useful tool to investigate treatment options for idiopathic pulmonary fibrosis?", vol. 40, pp. 362-382, 2008.
Clavel et al., "Synthesis and biological activity of M6-P and M6-P analogs on fibroblast and keratinocyte proliferation," vol. 60, pp. 721-725, 2005.
International Search Report of International Application No. PCT/IB2010/00960.

*Primary Examiner* — Shaojia Anna Jiang
*Assistant Examiner* — Michael C Henry
(74) *Attorney, Agent, or Firm* — Venable LLP; Keith G. Haddaway; Daniel A. Kopp

(57) ABSTRACT

Methods of using phosphotetrahydropyran compounds for treatment of fibrotic and scarring disorders, e.g. pulmonary fibrosis, fibrosis associated with surgical procedures, wound healing disorders, scar formation, sclerotic disorders, ocular fibrotic disorders, ocular healing disorders, ocular fibrosis after surgery, glaucoma, tendon scarring disorders, joint scarring disorders, kidney interstitial fibrosis and glomerular fibrosis and tubular fibrosis of the kidney.

20 Claims, 5 Drawing Sheets

Compound of Formula 1; n = 1 and R = 2,4-dimethylphenyl

Compound of Formula 1; n = 1 and R = 2,4-dimethylphenyl

PHOSPHOTETRAHYDROPYRAN COMPOUNDS FOR THE TREATMENT OF WOUNDS AND FIBROTIC DISORDERS

FIELD OF THE INVENTION

This invention relates to phosphotetrahydropyran compounds and methods to treat fibrotic and scarring disorders, e.g. pulmonary fibrosis, fibrosis associated with surgical procedures, wound healing disorders, scar formation, sclerotic disorders, ocular fibrotic disorders, ocular healing disorders, ocular fibrosis after surgery, glaucoma, tendon scarring disorders, joint scarring disorders, kidney interstitial fibrosis and glomerular fibrosis and tubular fibrosis of the kidney.

BACKGROUND

Fibrotic processes are associated with a wide range of physiological disorders. Scarring can be problematic in nearly all organs and tissues of the body, e.g. eyes, lungs, central nervous system, muscle, joints, kidney etc. Similar processes may also result in other fibrotic disorders which are common in many areas of medicine and surgery. For example, abdominal surgery often leads to intraperitoneal fibrous adhesions and/or strictures, whilst fibrotic retinopathy, scarring following glaucoma surgery, fibrosis of the trabecular meshwork, proliferative vitreoretinopathy, keloids and hypertrophic scars, skin diseases (e.g. epidermolysis bullosa, scleroderma), systemic sclerosis, pulmonary fibrosis, glomerulo nephritis, tubule-interstitial kidney fibrosis, myocardial fibrosis after myocardial infarct, scarring of the central nervous system following, for example a stroke or neurosurgery and hepatic cirrhosis are significant medical problems. Inappropriate scarring can compromise joint function after tendon damage.

Adult wound healing is characterised by acute inflammation, contraction and collagen deposition, responses likely to have been optimised for rapid wound closure and minimising infection. In brief, when the human body or the body of any mammal is wounded, a set of complex biochemical events takes place to repair the damage. These events start with an inflammatory phase which leads to the release of cytokines that cause the migration and division of cells involved in the proliferative phase. At this stage collagen deposition, granulation tissue formation, epithelialization, and wound contraction are observed. Fibroblasts grow and form a new, provisional extracellular matrix (ECM) by excreting collagen and fibronectin. Epithelial cells migrate and cover the wound, and then the wound is made smaller by the contraction of myofibroblasts. Finally in the remodeling phase, collagen is remodeled and realigned along tension lines and cells that are no longer needed are removed by apoptosis.

Inflammation and pro-fibrotic molecules induce the transformation of epithelial cells into mesenchymal cells (EMT), promoting the accumulation of fibroblasts and myofibroblasts, fibrosis and migration of activated mesenchymal cells to expand the fibrotic foci. This process of cellular transdifferentiation is largely regulated by transforming growth factor-beta (TGF-beta).

In most cases, wound healing leads to the formation of well constructed scar tissue. However, in cases when one or more steps in this cascade are not well regulated serious consequences to health and appearance may result. These may arise from aberrant deposition of collagen and fibronectin which is observed in scleroderma and idiopathic pulmonary fibrosis and many related disorders, for example. Furthermore, aberrant tissue repair may occur after surgical procedures, including eye surgery, abdominal surgery, spinal surgery and the repair of surface wounds leading to keloid formation. It may be necessary to attenuate normal tissue repair in some instances; for example after a surgical procedure to drain aqueous humor from the eye, the scarring process can prematurely close the small drainage hole. Systemic diseases including diabetes and hypertension could induce injury of the glomerular and tubular cells in the kidney resulting in kidney fibrosis and renal failure.

The scarring process can be understood from a biochemical perspective as a TGF-beta initiated cascade of events. TGF-beta derives from latent transforming growth factor-beta (LTGF-beta). Thus the activation of LTGF-beta to active TGF-beta is a critical step in the healing and fibrotic processes. LTGF-beta (which comprises TGF-beta bound to the latency associated peptide (LAP), which in turn may be bound to the LTGF-beta binding protein (LTBP)), binds to cell-surface cation-independent mannose-6-phosphate (CI-M6P) receptors through the recognition of M6P-modified amino acids in the LAP. This binding allows the activation of the LTGF-beta initiated by a cascade of events which ultimately lead to the release of TGF-beta.

Since LTGF-beta binds to the CI-M6P receptor, CI-M6P receptor antagonists can play a significant role in the healing process by competing with the M6P-containing carbohydrates in the LAP for the CI-M6P receptor binding site. By acting in this way phosphotetrahydropyran CI-M6P receptor antagonists can attenuate or completely inhibit the binding of LTGF-beta to the M6P receptor, and the levels of active TGF-beta will be reduced.

Connective tissue growth factor (CTGF) is a secreted cytokine believed to be a central mediator in these cellular processes. In particular, CTGF is known to increase extracellular matrix production via increased deposition of collagen and fibronectin. Over-expression of CTGF has been implicated as a major causative factor in conditions such as scleroderma, fibroproliferative diseases, and scarring in is which there is an over accumulation of extracellular matrix components.

It has been reported that transforming growth factor beta (TGF-beta) and connective tissue growth factor (CTGF) are over-expressed in a coordinated fashion in an in vivo model of wound repair, suggesting that TGF-beta-stimulated CTGF expression is involved in the healing of wounds. In a mouse model of skin fibrosis the subcutaneous injection of TGF-beta or CTGF had only minor effects when administered alone, but when together, a more persistent fibrotic response was observed. Therefore it is likely that CTGF acts as a downstream effector of TGF-beta acting to enhance the production of scar tissue. It has also been shown that inhibition of CTGF expression by antisense mRNA or by CTGF-binding antibodies prevents increased collagen synthesis in fibroblasts exposed to TGF-beta suggesting that CTGF induction is essential for the fibrotic response to TGF-beta. Suppression of CTGF might prevent a progressive fibrotic response to stimulation by TGF-beta.

Increased levels of TGF-beta, induced by inflammation, high glucose, hypoxia or other types of injury, are implicated in the modulation of a variety of cellular and molecular processes leading to cell activation, proliferation and migration. TGF-beta modulates molecular interactions with MAPK, PI3K/Akt, Wnt, Hedgehog, Notch and HIF pathways in a complex and context-dependent crosstalk cell signalling pathway.

Many of these fibrotic diseases and scarring disorders are very poorly treated with current medication, one example being idiopathic pulmonary fibrosis (IPF). IPF is a chronic lung disease of unknown origin characterised by chronic progressive interstitial lung fibrosis causing dyspnoea due to poor gas exchange and non-productive cough. Classically a disease of adulthood, IPF has a poor prognosis and no proven effective treatment. IPF is usually fatal with a life expectancy of three years after diagnosis, with cor pulmonale and cardiac failure being the main causes of death. Histopathological examination evidences alveolar damage with aberrant epithelial repair and interstitial pneumonia with overproduction of collagen, fibronectin and other ECM components by activated fibroblasts.

IPF development has been strongly correlated with cigarette smoking, and exposure to either silica or livestock. Other studies have suggested a correlation with viral infections. While the etiology of the disease remains to be understood, the pathogenesis seems to follow a model initiated by alveolar epithelial cell injury resulting in release of pro-inflammatory mediators as well as fibroblast proliferation similar to the process normally seen during tissue repair and would healing. In IPF patients, the lung injury cycle persists and the repair process never resolves, resulting in progressive fibrosis and loss of normal lung tissue architecture.

Acute inflammation of alveolar tissue has been proposed to be the first stage of IPF. This inflammatory process, started with an initial injury, is characterized by the acute recruitment of neutrophils and followed by migration of monocytes, lymphocytes and other immune-cells into the alveolar space. This induces epithelial and fibroblast activation accompanied by release of inflammatory mediators where TGF-beta, TNF and platelet derived growth factor play important roles. In susceptible individuals, acute inflammation does not resolve and gives rise instead to chronic inflammatory changes, abnormal alveolar tissue repair and remodeling which results in progressive fibrosis. Fibrogenic cytokines, including TGF-beta and TNF, induce myofibroblast migration and accumulation in the lung tissue, which in turn promote extracellular matrix deposition, collagen accumulation and other features of the fibrotic component of IPF.

There is an urgent need for medication to control both the initial inflammatory insult as well as the subsequent sequelae of fibrolytic and scarring events in patients suffering from IPF.

The eye is a very sensitive organ that is prone to injury and tissue tear and is frequently subjected to surgical procedures. In all instances aberrant wound repair can lead to ocular disorders; these are associated with inflammatory and cellular processes described previously. An over accumulation of extracellular matrix materials in the region of the trabecular meshwork (TM) is observed in forms of glaucoma; such increases are believed to lead to increased resistance to aqueous outflow and, therefore, elevated intraocular pressure (IOP).

The TM is a complex tissue including trabecular cells, connective tissue, and extracellular matrix located at the angle between the cornea and iris that provides the normal resistance required to maintain a normal IOP. An adequate IOP is needed to maintain the shape of the eye and to provide a pressure gradient to allow for the flow of aqueous humor to the avascular cornea and lens. Excessive IOP, commonly present in glaucoma, has deleterious effects on the optic nerve, leads to loss of retinal ganglion cells and axons, and results in progressive visual loss and blindness if not treated. Glaucoma is one of the leading causes of irreversible visual impairment and blindness worldwide.

Most forms of glaucoma result from disturbances in the flow of aqueous humor that have an anatomical, biochemical or physiological basis. Primary open angle glaucoma (POAG), also known as chronic or simple glaucoma, represents the majority of all glaucomas in the United States. POAG is characterized by pathological changes in the TM, resulting in abnormally high resistance to fluid drainage from the eye. A consequence of such resistance is an increase in the IOP.

Current anti-glaucoma therapies lower IOP by the use of medications to suppress aqueous humor formation or to enhance aqueous outflow. Unfortunately, the use of drug therapy alone is not sufficient to adequately control intraocular pressure in, some patients, particularly if there is a severe blockage of the normal passages for the outflow of aqueous humor. Such patients may require surgical intervention to restore the normal outflow of aqueous humor and thereby normalize or at least control their intraocular pressure. The outflow of aqueous humor can be improved by means of various intraocular surgical procedures, such as trabeculectomy, posterior lip sclerectomy, trephine and thermal sclerostomy. These surgical procedures are collectively referred to herein as glaucoma filtration surgery (GFS).

GFS, in particular a guarded sclerostomy procedure otherwise known as trabeculectomy, is a key point in the long term management of a patient's disease. Glaucoma surgery is traditionally performed on patients who have uncontrolled intraocular pressures (IOP) whilst on maximally tolerated medical treatment, or after failed laser trabeculoplasty and requires the surgeon to have great control over post-operative scarring to control the potential visual loss which can occur from glaucomatous damage if the intraocular pressures are not adequately controlled.

The procedures utilized in glaucoma filtration surgery generally involve the creation of a fistula to promote the drainage of aqueous humor. Although various procedures have been utilized, the procedures will typically include the creation of an elevation of the conjunctiva at the surgical site. This elevation is commonly referred to as the "filtering bleb". The filtering blebs which are most often associated with good intraocular pressure control are avascular and either low and diffuse or elevated with numerous cystic spaces. Studies have suggested that aqueous fluid in the filtering bleb usually filters through the conjunctiva and mixes with the tear film, or is adsorbed by vascular or perivascular conjunctival tissue. Although glaucoma filtration surgery is generally successful initially, it is often plagued by the formation of scar tissue which may ultimately block the fistula created during the surgery. Increased amount of collagen in the failed fistulas suggests that proliferation of fibroblasts and associated production of extracellular matrix materials, particularly collagen, fibronectin and glycosaminoglycans were observed.

In order to prevent the scarring process the use of antimetabolite/antifibrotic drugs has emerged as an important adjunct to glaucoma filtration surgery. Among the different drugs tested the following are the ones most frequently used at present. 5-Fluorouracil (5-FU) is a pyrimidine analogue that acts by selectively inhibiting DNA synthesis in the S and the G2 phases of the cell cycle. Mitomycin C (MCC) acts by reducing fibroblast collagen synthesis through, inhibition of DNA-dependant RNA synthesis and has a direct cytotoxic effect. However, there are serious complications with current treatments including corneal epithelial toxicity, increased conjunctival wound leak frequency, hypotony and hypotony maculopathy, increased incidence of suprachordial hemorrhage, accurate dosimetry due to variability of delivery of drug between impregnated sponge and subconjunctival tissues, leakage away from treatment site leading to extra/intra ocular toxicity, and high levels of cell apoptosis.

Due to these limitations with current drug regimens, there is an urgent need for new methods to control both the initial inflammatory insult as well as the subsequent sequelae of scarring events to better preserve the filtering bleb.

Another unmet medical need is the control of excessive cutaneous scarring that causes functional, cosmetic and psychological morbidity. Clinical scar management after trauma, surgical injury or burns involves consideration of both the continual physical assessment of the scar, including bodylocation and the patient's previous scar history, with a clinical regimen that is often modulated over the course of treatment. Accepted conservative treatments for hypertrophic scars and keloids are limited to surgery, corticosteroid injections, radiotherapy, silicone gel sheeting and pressure therapy. Treatments that specifically target the biological mechanisms responsible for hypertrophic scars and keloids would complement existing therapy and could improve current scar outcome.

Cutaneous scarring, which is described as macroscopic disruptions of normal skin architecture and function, arises as a consequence of wound repair and proceeds as a fibroproliferative response. Keloids are hallmarked by growth beyond the margins of the original trauma site, are associated with familial disposition, and rarely regress. Hypertrophic scars are raised, erythematous fibrous lesions which usually undergo resolution over time and are associated with contracture of tissue.

In view of the serious consequences when the wound healing process goes awry, there is an urgent need for new medicines to control one or more steps of the cascade of biochemical events. Most appealing would be methods to modulate both the initial and ongoing inflammatory events and the subsequent collagen and fibronectin deposition. Where the human disease or disorder is well established, such methods are therapeutic leading to amelioration of disease symptoms. However, such methods can also be used prophylactically when administered at the time of surgical intervention and for defined periods following surgery.

Renal function impairment and progression to kidney failure are serious consequences of chronic systemic diseases including type 2 diabetes and hypertension. In type 2 diabetes, disruption of the glomerular filtering function and thickening of the tubular apparatus driven by high glucose levels in serum and tissue hypoxia lead to progressive renal function impairment and almost inevitable late stage renal failure driven by fibrotic tissue deposition in the renal parenchyma. Lack of effective therapeutic agents make this field an unmet medical need.

SUMMARY

In one aspect, the present invention provides for a method to improve the healing of wounds or alleviation of fibrotic disorders, resulting in reduced or improved scarring, comprising the use of phosphotetrahydropyran compounds. By "wounds or fibrotic disorders" is meant any condition which may result in the formation of scar or fibrotic tissue.

In one embodiment, a method of treating pulmonary fibrosis (lung fibrosis) is provided. Treatment is effected by administering an effective amount of a phosphotetrahydropyran compound, or a prodrug or salt thereof, as described herein, to an individual in need of treatment, using a suitable route of administration, such as, but not limited to intravenous administration, oral administration, local administration, and inhalation. The compounds, prodrugs or salts to be administered will typically be in the form of a pharmaceutical composition, optionally including pharmaceutically acceptable excipients and/or carriers.

Chemical Structures

Figure 1:
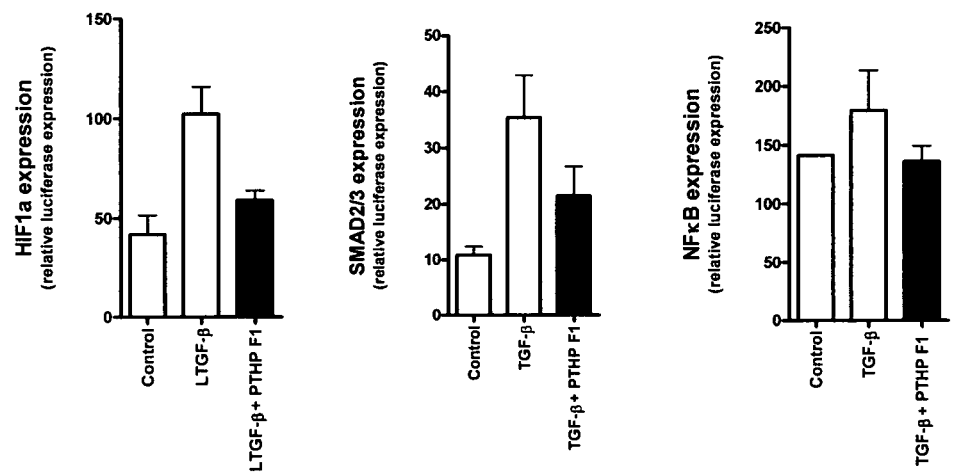
FIG. 1 illustrates that a phosphotetrahydropyran test compound at concentrations ranging from 0.01 µM to µM effectively reduced activation of NFkB, HIF1a and SMAD signaling pathways.

The central chemical entity upon which the novel compounds of the present invention are based is shown in Formula I, below:

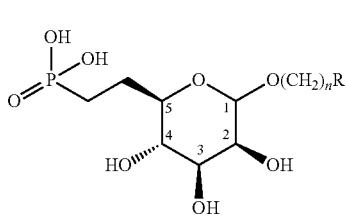

Formula I wherein n is an integer from 0 to 3, the —O(CH$_2$)$_n$R group is in an axial or equatorial position, and R is lower alkyl, or optionally substituted heteroaryl or optionally substituted aryl wherein the substituent is selected from the group consisting of —Cl, —F, CF$_3$, CH$_3$, CH$_2$CH$_3$, —OCH$_3$, —OCF$_3$, —(CH$_2$)$_m$CO$_2$R$^1$, —(CH$_2$)$_m$OR$^2$, —(CH$_2$)$_m$CONHR$^2$, —(CH$_2$)$_m$NHR$^2$, and —(CH$_2$)$_m$CONR$^2$R$^3$, wherein m is an integer from 0 to 3; $R^1$ is selected from the group of consisting of H, alkyl and aryl; and $R^2$ and $R^3$ are independently selected from the group consisting of H, alkyl, aryl and acyl.

This genus of compounds is referred to as the "Formula I compounds". Also included are salts, hydrates, derivatives and prodrugs of the above Formula I compounds.

The term "alkyl", denotes straight chain, branched or cyclic fully saturated hydrocarbon residues. Unless the number of carbon atoms is specified the term preferably refers to $C_{1-6}$ alkyl which is also referred to as "lower alkyl." When "alkyl" groups are used in a generic sense, e.g., "propyl," "butyl", "pentyl" and "hexyl," etc., it will be understood that each term may include all isomeric forms (straight, branched or cyclic) thereof. A preferred alkyl is $C_{1-4}$ alkyl; more preferred is $C_{1-3}$ alkyl. Examples of straight chain and branched $C_{1-5}$ alkyl include methyl, ethyl, n-propyl, isopropyl, n-butyl, sec-butyl, tert-butyl, n-pentyl, iso-pentyl, 1,2-dimethylpropyl, 1,1-dimethylpropyl. Example of cycloalkyl groups are cyclopropyl, cyclopropylmethyl, cyclopropylethyl, cyclobutyl, cyclopentyl, cyclohexyl, etc.

An alkyl group, as defined herein, may be optionally substituted by one or more substituents. Suitable substituents may include: halo (fluoro, chloro, bromo or iodo); haloalkyl (e.g., trifluoromethyl, trichloromethyl); hydroxy; mercapto; phenyl; benzyl; amino; alkylamino; dialkylamino; arylamino; heteroarylamino; alkoxy (e.g., methoxy, ethoxy, butoxy, propoxy phenoxy; benzyloxy, etc.); thio; alkylthio (e.g., methyl thio, ethyl thio); acyl, for example acetyl; acyloxy, e.g., acetoxy; carboxy (—$CO_2H$); carboxyalkyl; carboxyamide (e.g., —CONH-alkyl, —CON(alkyl)$_2$, etc.); carboxyaryl and carboxyamidoaryl (e.g., CONH-aryl, —CON(aryl)$_2$); cyano; or keto (where a $CH_2$ group is replaced by C=O).

The terms "alkoxy" and "acyloxy" refer to alkyl and acyl groups respectively when linked by oxygen.

As used herein the term "alkenyl" denotes groups formed from straight chain, branched or cyclic hydrocarbon residues containing at least one C=C double bond including ethylenically mono-, di- or poly-unsaturated alkyl or cycloalkyl groups as previously defined. Thus, cycloalkenyls are also intended. Unless the number of carbon atoms is specified, alkenyl preferably refers to $C_{2-20}$ alkenyl. More preferred are lower alkenyls ($C_{2-6}$), preferably $C_{2-5}$, more preferably $C_{2-4}$ or $C_{2-3}$. Examples of alkenyl and cycloalkenyl include ethenyl, propenyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. Preferred alkenyls are straight chain or branched. As defined herein, an alkenyl group may optionally be substituted by the optional substituents described above for substituted alkyls.

As used herein the term "alkynyl" denotes groups formed from straight chain, branched or cyclic hydrocarbon residues containing at least one C≡C triple bond including ethynically mono-, di- or poly-unsaturated alkyl or cycloalkyl groups as previously defined. Unless the number of carbon atoms is specified, the term refers to $C_{2-20}$ alkynyl. More preferred are lower alkynyls ($C_{2-6}$), preferably $C_{2-5}$, more preferably $C_{2-4}$ or $C_{2-3}$ alkynyl. Examples include ethynyl, 1-propynyl, 2-propynyl, butynyl (including isomers), and pentynyl (including isomers). A particularly preferred alkynyl is a $C_{2-6}$ alkynyl. Preferred alkynyls are straight chain or branched alkynyls. As defined herein, an alkynyl may optionally be substituted by the optional substituents described above for alkyl.

The term "acyl" denotes straight chain or branched alkanoyl (C(O)alkyl), alkenoyl (C(O)alkenyl) or alkynoyl (C(O)alkynyl). Preferred alkanoyls are ethanoyl (=acetyl), propanoyl, n-butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl. Examples of alkenoyls are propenoyl, butenoyl, pentenoyl, palmitoyl, oleoyl and lineoyl. The hydrocarbon chain of an acyl may optionally be further substituted by one or more substituents as described above, so that "acyl" is also intended to refer to a substituted acyl.

The term "aryl" denotes a single, polynuclear, conjugated or fused residue of an aromatic hydrocarbon ring system. Examples of aryl are phenyl, biphenyl and naphthyl. An aryl group may be optionally substituted by one or more substituents as herein defined. Accordingly, "aryl" as used herein also refers to a substituted aryl.

The term "heteroaryl" denotes a single, polynuclear, conjugated or fused aromatic heterocyclic ring system, wherein one or more carbon atoms of a cyclic hydrocarbon residue is substituted with a heteroatom to provide a heterocyclic aromatic residue. Where two or more carbon atoms are replaced, the replacing atoms may be two or more of the same heteroatom or two different heteroatoms. Suitable heteroatoms include O, N, S and Se. Examples of heteroaryls include pyridyl, 4-phenylpyridyl, 3-phenylpyridyl, thienyl, furyl, pyrrolyl, indolyl, imidazolyl, oxazolyl, pyridazinyl, pyrazolyl, pyrazinyl, thiazolyl, pyimidinyl, quinolinyl, isoquinolinyl, benzofuranyl, benzothienyl, purinyl, quinazolinyl, phenazinyl, acridinyl, benoxazolyl, benzothiazolyl and the like. As defined herein, a heteroaryl group may be optionally further substituted by one or more substituents as described above.

As used herein the term "aralkyl" denotes the group —Ar—R', wherein Ar is an aryl group and R' is lower alkyl or substituted lower alkyl group. Aryl groups can optionally be substituted at other positions with, e.g., halo, lower alkyl, alkoxy, alkylthio, lower alkenyl, lower alkynyl, amino, amido, carboxyl, hydroxyl, aryl, aryloxy, heterocycle, substituted heterocycle, heteroaryl, substituted heteroaryl, nitro, cyano, thiol, sulfamido and the like. Examples of aralkyl compounds include aromatic compounds having a divalent halomethyl group, hydroxymethyl group, and alkoxymethyl group.

In one preferred embodiment, R in formula I is a substituted aryl group which is substituted by one or more halogen, alkyl, carboxy, amido or amino groups, for example, —Cl, —F, —$CH_3$, —$CH_2CH_3$, —$(CH_2)_mCO_2R^1$, —$(CH_2)_mOR^2$, —$(CH_2)_mCONHR^2$, —$(CH_2)_mNHR^2$, —$(CH_2)_mCONR^2R^3$ or —$(CH_2)_m CONR^2R^3$ wherein m=0-3, $R^1$ is H, alkyl or aryl, and wherein $R^2$ or $R^3$, independently, is H, alkyl, aryl or acyl.

Other preferred R groups in formula I include: phenyl; 2-methylphenyl; 2,4-dimethylphenyl; 2,4,6-trimethylphenyl; 2-methyl, 4-chlorophenyl; aryloxyalkyl (e.g., phenoxymethyl or phenoxyethyl); benzyl; phenethyl; 2, 3 or 4-methoxyphenyl; 2, 3 or 4-methylphenyl; 2, 3 or 4-pyridyl; 2, 4 or 5-pyrimidinyl; 2 or 3-thiophenyl; 2,4, or 5-(1,3)-oxazolyl; 2, 4 or 5-(1,3)-thiazolyl; 2 or 4-imidazolyl; 3 or 5-symtriazolyl.

The term "salt, derivative or prodrug" includes any pharmaceutically acceptable salt, ester, solvate, hydrate or other compound which, upon administration to a subject, is capable of generating (either directly or indirectly) a compound as described herein. However, it will be appreciated that pharmaceutically "unacceptable" salts also fall within the scope of the invention since these may be used to prepare pharmaceutically acceptable salts. Suitable pharmaceutically acceptable salts include, but are not limited to, salts of pharmaceutically acceptable:

(a) inorganic acids such as hydrochloric, sulfuric, phosphoric, nitric, carbonic, boric, sulfamic, and hydrobromic, or
(b) organic acids such as acetic, propionic, butyric, tartaric, maleic, hydroxymaleic, fumaric, maleic, citric, lactic, mucic, gluconic, benzoic, succinic, oxalic, phenylacetic, methanesulfonic, toluenesulfonic, benezenesulfonic, salicylic sulfanilic, aspartic, glutamic, edetic, stearic, palmitic, oleic, lauric, pantothenic, tannic, ascorbic and valeric.

Base salts include, but are not limited to, those formed with pharmaceutically acceptable cations, such as sodium, potassium, lithium, calcium, magnesium, ammonium and alkylammonium. In particular, cationic salts are within the scope of this invention, e.g., sodium or potassium salts; also included are alkyl (e.g., methyl, ethyl) phosphoesters. Preferred salts are alkali metal salts of the phosphonate functional group, and more preferred are the calcium and the mono and bis sodium salts.

Basic nitrogen-containing groups may be quaternized using: (1) a lower alkyl halide, such as methyl, ethyl, propyl or butyl chloride, bromide or iodide; (2) dialkyl sulfates, e.g., dimethyl or diethyl sulfate; and others.

The compounds of the invention may be in amorphous or crystalline forms either as the free compounds or as solvates (e.g., hydrates) both of which classes are within the scope of this invention. Methods of solvation are routine in the art. The preferred solvate is water which may be present from 2 to 20%.

Any prodrug of a compound of formula I is within the scope and spirit of the invention. The term "pro-drug" is used in its broadest sense to encompass those derivatives that are converted in vivo to the compounds of the invention. Such derivatives are readily apparent to those skilled in the art, and include, for example, compounds in which (1) a free hydroxy group is converted into an ester (such as an acetate), or (2) a free amino group is converted into an amide. Procedures for acylating the compounds of the invention are well known in the art and include reaction with an appropriate carboxylic acid, anhydride or chloride in the presence of a suitable catalyst or base. Preferred prodrugs are mono and diesters of phosphonic acid functionality, more preferred are oxymethylene spaced esters shown in Formula II in which X is a hydrogen or substituted alkyl, and most preferred is a diester in which X is hydrogen and Px is tert-butyl. Procedures for the preparation of these phosphonic acid derivatives are well known in the chemical literature, for example in Baudy, R.B. et al., Journal of Medicinal Chemistry, 52, 771-778 (2009).

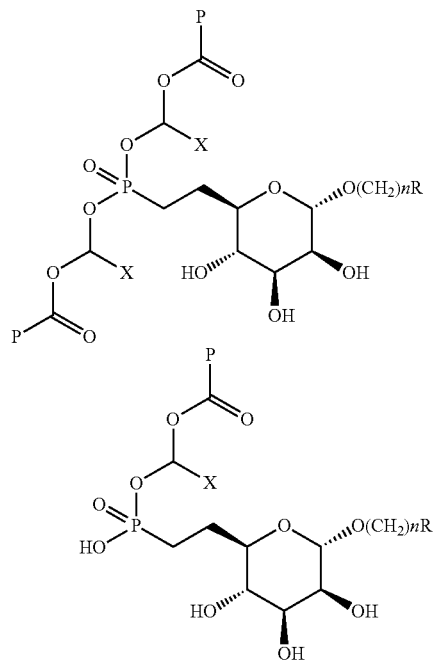

The compounds of this present invention described by Formula 1 can be prepared by routes described in the patent application WO 2004/104 015.

Also provided is a method comprising the use of such compounds either immediately before or immediately after a surgical procedure to promote reduced or improved scarring.

The method may be used in conjunction with other methods known in the art for promoting the healing of wounds with reduced scarring or treating fibrotic disorders. Numerous compounds have shown activity in the bleomycin animal model of pulmonary fibrosis and many of these will work additively or synergistically with compounds of the present invention to lead to a better therapeutic outcome; these are described in Moeller A., et al. The International Journal of Biochemistry and Cell Biology, 40, 362-382 (2008). Specific examples are: N-acetyl cysteine, aminoguanidine, anti-VEGF antibody, Batimastat, Bosentan, dexamethasone, difluoromethylornithine, Etanercept, Gefitinib, Imatinib, methylprednisolone, Pentoxifylline, Pirfenidone, prednisolone, Rosiglitazone, TGF-beta antibody, TNF-alpha antibody, and Vinblastine.

The compounds and compositions of the present invention may be administered by any appropriate and effective route as determined by the skilled practitioner. Suitable routes of administration are described, for example in Remington: The Science and Practice of Pharmacy, University of the Sciences in Philadelphia (2005). For example, the compounds may be administered intravenously, topically, orally, intramuscularly, intradermally, by inhalation or subcutaneously.

To treat patients suffering from a lung fibrosis condition, the preferred routes of administration are oral and locally by inhalation. Inhaled compounds of the present invention can be formulated for use with dry powdered inhalers, metered dose inhalers or as a solution for nebulisation. Oral compounds of the present invention can be formulated as a capsule, tablet or solution.

To treat patients suffering from cardiac scarring the preferred routes of administration are oral, intravenous, subcutaneous and as a coated stent to be implanted by a surgeon.

To treat patients who have undergone eye surgery, or who have suffered wounds to the eye, or who have glaucoma, the preferred routes of administration are oral, intravenous, by injection directly into the affected region of the eye, as eye drops, by soaking into a sponge and being applied to the wound at the time of surgery, and contained within in an implant which is surgically introduced.

To treat patients who have undergone spinal and back surgery, the preferred rout of administrations are oral, intravenous, and direct application to the wound during surgery as a powder, solution or soaked into a sponge.

To treat patients suffering from scleroderma, kidney fibrosis, and other fibrotic conditions, the preferred routes of administration are oral, intravenous, and coated implants.

For patients who have undergone plastic surgery, or who are prone to keloid formation, or who have skin burns, the preferred route of administration is as an ointment or a cream, or injected directly to the site of the wound, oral or intravenous, For patients suffering from injury to tendons, including tendons in the hands, shoulders, elbows, hips, knees and feet, Dupuytren's disease, frozen shoulder (adhesive capsulitis), the preferred routes of administration are local injection, as an ointment or cream, or administered directly to the site of the wound, oral or intravenous, Compounds will be formulated suitably according to the route of administration, for example, in liquid or particle form suitable for inhalation, in solutions for injection, as an ointment or cream for application directly to the skin, etc. Dosages can be determined by the ordinarily skilled practitioner without undue experimentation. For intravenous administration doses from 1 to 1000 mg of compound are preferred; more preferred are doses from 5 to 100 mg. For oral administration, a phosphonate diester prodrug form of the inventive compounds is preferred with doses in the range of 5 to 4000 mg, more preferably 10 to 500 mg. For injection directly to the site of the wound, concentrations of 0.1 to 1000 millimolar are preferred; more preferred are doses of 0.1 to 100 millimolar. When administered as an ointment or cream, a phosphonate diester prodrug form of the inventive compounds is preferred with doses in the range of 50 to 4000 mg, more preferably 50 to 500 mg.

As used herein, the term "subject" is intended to mean a mammal, in particular a human. Usually the subject will be afflicted with a disease, wound or disorder that is expected to be alleviated using the treatment methods described herein. Some examples of diseases and disorders are listed below.

An "effective amount" of a compound or composition is one that will produce a measurable effect in alleviating at least one symptom of the disease or disorder being treated. It is not necessary that said symptoms be completely alleviated.

The present invention provides a method for attenuating TGF-beta signalling in an eye of a subject by providing phosphotetrahydropyran antagonists of the CI-M6P receptor. A method of attenuating TGF-beta signalling in an eye of a subject comprises administering to the subject a composition comprising an effective amount of a phosphotetrahydropyran or a pharmaceutically acceptable salt or prodrug thereof, and a pharmaceutically acceptable carrier. The TGF-beta signalling-associated ocular disorder may be ocular hypertension, glaucoma, glaucomatous retinopathy, optic neuropathy, macular degeneration, diabetic retinopathy, choroidal neovascularization, or proliferative vitreoretinopathy, for example.

Another embodiment of the invention is a method of treating a TGF-beta signalling-associated ocular disorders associated with inappropriate transforming growth factor signalling in a subject in need thereof. The method comprises administering to the subject a composition comprising an effective amount of a phosphotetrahydropyran antagonist of the CI-M6P receptor or a pharmaceutically acceptable salt or prodrug thereof, and a pharmaceutically acceptable carrier.

Also provided is a method comprising the use of such phosphotetrahydropyran compounds either immediately before or immediately after a surgical procedure to reduce the scarring process following glaucoma filtration surgery.

In another embodiment of the present invention a method of treating glaucomatous retinopathy, optic neuropathy, macular degeneration, diabetic retinopathy, choroidal neovascularization, proliferative vitreoretinopathy, or cataracts and other fibrotic conditions of the lens in a subject is provided. The method comprises administering to the subject a composition comprising an effective amount of a phosphotetrahydropyran antagonist of the CI-M6P receptor or a pharmaceutically acceptable salt or prodrug thereof, and a pharmaceutically acceptable carrier.

Another embodiment of the invention is a method to treat the inflammation component of fibrotic ocular disorders associated with inappropriate transforming growth factor signalling in a subject in need thereof. The method comprises administering to the subject a composition comprising an effective amount of a phosphotetrahydropyran antagonist of the CI-M6P receptor or a pharmaceutically acceptable salt or prodrug thereof, and a pharmaceutically acceptable carrier.

Also provided is a method comprising the use of such phosphotetrahydropyran compounds either immediately before or immediately after a surgical procedure to attenuate the inflammation process which initiate the scarring process following glaucoma filtration surgery.

Another embodiment of the invention is a method of treating fibrotic lung disorders associated with inappropriate transforming growth factor signalling in a subject in need thereof. The method comprises administering to the subject a composition comprising an effective amount of a phosphotetrahydropyran antagonist of the CI-M6P receptor or a pharmaceutically acceptable salt or pro-drug thereof, and a pharmaceutically acceptable carrier. The TGF-beta signalling-associated lung disorder may be idiopathic pulmonary fibrosis, or other interstitial lung diseases (ILD) of adulthood and childhood of unknown origin including chronic interstitial pneumonia, descamative interstitial pneumonitis, usual interstitial pneumonitis, non-specific interstitial pneumonitis, sarcoidosis, lymphocytic interstitial pneumoitis, Lymphangiomatosis, nonadenoviral bronchiolitis obliterans, Idiopathic bronchiolitis obliterans organizing pneumonia, bronchocentric granulomatosis, nonspecific interstitial pneumonia and acute interstitial pneumonitis as well as ILD of known origin including infection, environmental exposure, drug induced, metabolic disorders and immunodeficiency related ILD and other ILD associated with systemic diseases including connective tissue diseases, Autoimmune diseases, pulmonary vasculitis, liver and bowel disease, amyloidosis and neurocutaneous disorders.

Another embodiment of the invention is a method to treat patients suffering from tendon injuries or tendonitis. The disease can affect any joint in the body including but not restricted to hands, wrists, elbows, shoulders, spine, groin, knee, ankles and feet and results in loss of joint function or joint stiffness due to impaired tendon repair. The method comprises administering to the subject a composition comprising an effective amount of a phosphotetrahydropyran antagonist of the CI-M6P receptor or a pharmaceutically acceptable salt or prodrug thereof, and a pharmaceutically acceptable carrier.

Another embodiment of the invention is a method to treat patients suffering from poor or inappropriate wound healing after plastic surgery or other surgical inventions or wounds or burns to the skin. Examples are skin repair after a burn or after cosmetic surgery, or in the treatment or prevention of keloid formation. The method comprises administering to the subject a composition comprising an effective amount of a phosphotetrahydropyran antagonist of the CI-M6P receptor or a pharmaceutically acceptable salt or prodrug thereof, and a pharmaceutically acceptable carrier.

Another embodiment of the invention is a method to treat patients suffering from renal fibrosis. Glomerular and tubular fibrosis are a common manifestation of a variety of chronic diseases of the kidney. The method comprises administering to the subject a composition comprising an effective amount of a phosphotetrahydropyran antagonist of the CI-M6P receptor or a pharmaceutically acceptable salt or prodrug thereof, and a pharmaceutically acceptable carrier.

Another embodiment of the invention is a method to treat patients who have myocardial fibrosis. The disease affects individuals who have had heart injury including myocardial infarction, cardiac hypertrophy, open heart surgery, coronary artery disease, and others. The method comprises administering to the subject a composition comprising an effective amount of a phosphotetrahydropyran antagonist of the CI-M6P receptor or a pharmaceutically acceptable salt or prodrug thereof, and a pharmaceutically acceptable carrier.

Another embodiment of the invention is a method to treat patients suffering from localized or systemic fibrotic disorders, including the systemic and the cutaneous forms of scleroderma, morphea, neurofibromatosis, nephrogenic fibrotic disease, Dupuytren contracture and the similar. The method comprises administering to the subject a composition comprising an effective amount of a phosphotetrahydropyran antagonist of the CI-M6P receptor or a pharmaceutically acceptable salt or prodrug thereof, and a pharmaceutically acceptable carrier.

Another embodiment of the invention is a method to treat patients with excessive scar tissue formation after laminectomy or any other surgery on the spine. The method comprises treatment of post-surgical fibrosis of the epidural layer administering to the subject a composition comprising an effective amount of a phosphotetrahydropyran antagonist of the CI-M6P receptor or a pharmaceutically acceptable salt or prodrug thereof, and a pharmaceutically acceptable carrier.

DETAILED DESCRIPTION AND EXAMPLES

Example 1

Antagonism of Mannose 6-Phosphate Binding to the Cation-Independent Mannose 6-Phosphate Receptor All surface plasmon resonance (SPR) measurements were performed at 25° C. using a Biacore 3000 instrument (BIAcore, Piscataway, N.J.). CM5 research grade sensor chips, surfactant P20 and amine coupling kits were also obtained from BIAcore. Purified human β-glucuronidase was immobilized on CM5 sensor chips following activation of the surface using 1-ethyl-3-(3-dimethylaminopropyl)carbodiimide and N-hydroxysuccinimide as recommended by the manufacturer. Briefly, the proteins were injected onto the activated dextran surface at a concentration of 10-20 µg/mL in 10 mM sodium acetate buffer, pH 4.5 using 10 mM HEPES pH 7.5, 150 mM NaCl and 0.005% (v/v) P20 as the running buffer. After coupling, unreacted N-hydroxysuccinimide ester groups were blocked with ethanolamine. The reference surface was treated in the same way except that protein was omitted. Samples of purified sCI-MPR purified from fetal calf serum in 50 mM MES (2-(N-morpholino)ethanesulfonic acid), pH 6.5, 150 mM NaCl, 10 mM $MnCl_2$ and 5 mM 2-phosphoglycerol (MES buffer), supplemented with 0.005% (v/v) surfactant P20 and were injected in a volume of 80 or 90 µl over the coupled and reference flow cells at a flow rate of 40 mL/min (Trial 1) or 30 mL/min (Trial 2 and 3) respectively. After 2 min (Trial 1) or 3 min (Trial 2 and 3), the solutions containing the purified proteins were replaced with buffer and the complexes were allowed to dissociate for 2 min. The sensor chip surface was regenerated with a 10 µL injection of 10 mM HCl at a flow rate of 10 µL/min. The surface was allowed to re-equilibrate in running buffer for 1 min prior to subsequent injections. The response at equilibrium for each concentration of protein was determined by averaging the response over a 10 sec period within the steady state region of the sensorgram using the BIAevaluation software package (version 4.0.1). The response at equilibrium was plotted versus the log of the concentration of inhibitor and fitted by nonlinear regression to a one-site inhibition model using the equation $y=(min-max)/(1+10(x-\log K_i))$ SigmaPlot version 10.0, Systat Software, Inc.). All response data were triple-referenced, where controls for the contribution of the change in refractive index were performed in parallel and subtracted from all binding sensorgrams: 1) response from buffer alone; 2) response from the underivitized reference surface; 3) response from buffer containing matching concentration of mannose 6-phosphate (M6P) or the test phosphotetrahydropyran compound (Formula I). The mean $K_i$ values were determined to be between 1 and 20 µM for the phosphotetrahydropyran test compounds (Formula 1) and 19 µM for mannose-6-phosphate.

Under these conditions, compound of Formula 1 in which n=1 and R=2,4-dimethylphenyl was found to have a $K_i$ value of 7.9 µM.

Example 2

Inhibition of Myofibroblast Differentiation

Myofibroblast differentiation was determined using floating collagen gel cultures and quantitation of gel contraction. 24-Well tissue culture plates were pre-coated with bovine serum albumin. Trypsinized fibroblasts were suspended in MCDB medium (Sigma Aldrich) and mixed with collagen solution (1 part 0.2M HEPES [pH 8.0], 4 parts collagen [Vitrogen-100, 3 mg/ml], and 5 parts MCDB X2), yielding a final concentration of 80,000 cells per mL and 1.2 mg/mL collagen. Collagen/cell suspension (1 mL) was added to each well. After polymerization, gels were detached from wells by adding 1 mL MCDB medium. Contraction of the gel was quantified based on loss of gel weight and decrease in gel diameter over a 24-hour period. For inhibition experiments, cells were preincubated in the presence of the phosphotetrahydropyran test compound for 30 minutes prior to initiation of the assay. CTGF and alpha smooth muscle actin (αSMA) production was determined in whole cell protein extracts by Western blot analysis. Intensity of signals relative to GAPDH controls was calculated using densitometry, and averages and standard deviations of data obtained from 3 independent experiments were calculated. An $IC_{50}$ value for the phosphotetrahydropyran compound (Formula 1) was determined to be between 0.01 and 100 µM.

Example 3

Inhibition of Myofibroblast Differentiation in Human-Derived Fibroblasts

Dermal fibroblasts from affected areas in patients with systemic sclerosis and from age-, sex- and site-matched controls were used. Cells were grown in Dulbecco's modified Eagle's medium containing 5% fetal calf serum (FCS), 2 mM L-glutamine, antibiotics (100 units/mL penicillin and 100 μg/mL streptomycin), and 1 mM sodium pyruvate (Invitrogen, Burlington, Ontario, Canada). Cells were serum starved for 24 hours and then left untreated or treated with TGFβ1 (4 ng/mL). The phosphotetrahydropyran compound (Formula 1) at concentrations from 1 to 100 μM were added prior to the addition of TGFβ1. The CTGF and αSMA levels were determined 24 hours later in whole cell protein extracts by Western blot analysis. Under these conditions, the phosphotetrahydropyran compound (1) reduced CTGF and αSMA levels by 50% at concentrations between 0.01 and 100 μM.

Example 4

Inhibition of Extracellular Matrix Production

IMR-90 human fetal lung fibroblasts were plated on 25-sq cm flasks at a density of $1.5 \times 10^5$ cells. The cells were cultured in minimal medium containing 10% (v/v) newborn calf serum and either gentamicin (200 μg/mL) or chlortetracycline (100 μg/mL). Two antibiotics were alternately used so as not to select for bacteria which are resistant to either one. The cells were incubated at 37° C. in a humidified atmosphere of 5% $CO_2$ in air. For maintenance of cell cultures, the medium was changed every 72 hr. Cultured IMR 90 human lung fibroblasts and primary human fibroblasts isolated from lungs of patients with IPF were incubated in the presence of TGF-beta (5 ng/mL) and various concentrations of the phosphotetrahydropyran test compound (Formula 1). The production of extracellular matrix was assessed by mRNA quantification of fibronectin via Northern Blot analysis and confirmed real time PCR and compared to β-actin levels. The phosphotetrahydropyran test compound (Formula 1) reduced fibronectin product by 50% at concentrations between 0.01 and 100 μM.

Human proximal tubular (HK2) cells were exposed to high glucose (25 mM) and a range of the phosphotetrahydropyran compound (Formula I) concentrations from 0.1 μM to 100 μM in both normoxic and hypoxic (1% O2) conditions for 72 hours. Fibrotic markers including cellular and extra-cellular fibronectin, Collagen IV, E-cadherin, Vimentin, αSMA and MMPs were assessed by Western blotting and RNA amplification (real time PCR). Total and active TGFβ1 levels were detected using sensitive ELISA kits.

Test phosphotetrahydropyran compound (Formula I) at doses between 0.01 μM to 100 μM, effectively reduce the fibrotic signature in human proximal tubular cells stimulated with high glucose. The test phosphotetrahydropyran compound (Formula I) also reduces markers of epithelial to mesenchymal transformation (EMT) in these kidney cells.

Example 5

Combination Reagent Inhibition of Extracellular Matrix Production

Following the procedure described in Example 4, but treating IMR-90 human fetal lung fibroblasts with a combination of the phosphotetrahydropyran test compound (Formula 1) and one compound selected from N-acetyl cysteine, aminoguanidine, anti-VEGF antibody, Batimastat, Bosentan, dexamethasone, difluoromethylornithine, Etanercept, Gefitinib, Imatinib, methylprednisolone, Pentoxifylline, Pirfenidone, prednisolone, Rosiglitazone, TGF-beta antibody, TNF-alpha antibody, and Vinblastine, lower concentrations of both compounds were required to achieve the same reductions in fibronectin protein. For some combinations the effects were additive, while for others the effects were synergistic.

Example 6

Inhibition of Epithelial Mesenchymal Cell Transformation (EMT) in Rodent Cells

To assess the effect the phosphotetrahydropyran test compound (Formula 1) on epithelial mesenchymal transformation, rat lung epithelial cells were cultured in the presence of TGF-beta and the agent and alpha-smooth muscle actin assessed by western blotting.

Primary rat alveolar type II cells (AT2) were isolated from adult male Sprague-Dawley rats by elastase disaggregation (2.0-2.5 U/mL) followed by differential adherence on IgG-coated bacteriological plates as previously described. AT2 cells were then plated in a minimal defined serum-free medium (MDSF) on 1.1 cm2, 0.4 μm pore size uncoated polycarbonate filter cups (Transwell, Corning Costar, Cambridge, Mass.) at a density of 1×106 cells/cm2. For the first 24-48 hours in culture, media were supplemented with 100 μg/mL cis-OH-proline (Sigma) to selectively eliminate fibroblasts from cultures. Cultures were then maintained in a humidified 5% $CO_2$ incubator at 37° C. for up to 6 days. Media were changed daily and supplemented with combinations of TGF-β1 (1.0 ng/mL) and phosphotetrahydropyran test compound (Formula 1) at concentrations of 10, 30 or 100 μM. Inhibition of EMT was assessed by measuring the levels of CTGF, PGDF, or α-SMA after 24 hours. The compound (Formula 1) inhibited the TGF-beta1 induced stimulus by 50% at concentrations between 10 and 100 μM.

Example 7

Inhibition of Cell Signalling after TGF-Beta Stimulation

NIH-3T3 fibroblasts, IMR-90 cells and A549 cells were cultured in petri dishes. For transcription factor activation including HIF1a, NFkB, SMAD2/3, Notch, p53 MAPK/ERK pathways, cells were transfected using a firefly/renilla dual luciferase assay constructs. After transfection cells were incubated overnight in low serum medium containing 0.5% FCS supplemented with L-glutamine and antibiotics. Cells were then cultured in the presence or absence of increasing concentrations of phosphotetrahydropyran test compound (Formula 1) ranging from 0.01 μM up to 100 μM and stimulated with recombinant TGF-beta at concentrations ranging from 0.5 to 20 ng/mL or recombinant LTGF-beta at concentrations ranging from 5 to 50 ng/mL. Twenty four hours after stimulation cells were lysed and luminescence was measured to detect transcription factor activation.

Phosphotetrahydropyran test compound (Formula 1) at concentrations ranging from 0.01 μM to 100 μM effectively reduced activation of NFkB, HIF1a and SMAD signalling pathways. See FIG. 1.

Example 8

Activity in the Bleomycin Mouse Lung Damage Model (Model 1)

Male C57BU6 mice aged 8 weeks are housed on a 12 hour day/night cycle in micro-isolators cages. Food and water is allowed ad libitum.

A single Bleomycin challenge (5 mU/gram) in 50 µL of saline is instilled intratracheally on day 0. Control animals receive 50 µL of saline. Groups of animals are treated twice daily with phosphotetrahydropyran test compound (Formula 1) at various doses (i.p.) starting at day 0 for preventive therapy groups or day 7 for treatment therapy groups. Mice are studied for weight loss during the course of the experiment. At day 15 all mice are sacrificed and BALF is collected by tracheal cannulation for cell influx assessment in the lung airways. Total cell counts as well as phenotype are assessed. Lung histopathology including collagen deposition is assessed following standard methods.

Figure 2:
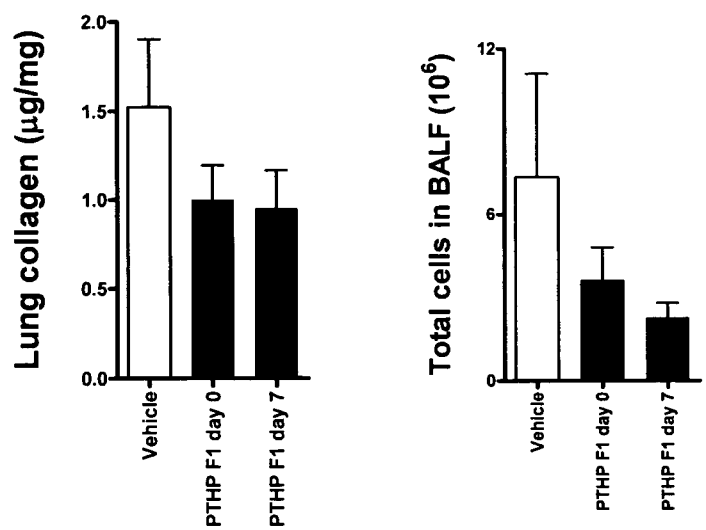
FIG. 2 illustrates that treatment with a phosphotetrahydropyran test compound effectively reduced total cell counts in BALF and decreased overall lung fibrosis determined by collagen deposition at doses between 1 and 100 mg/kg.

Treatment with phosphotetrahydropyran test compound (Formula 1) effectively improved weight gain, reduced total cell counts in BALF, and decreased overall lung fibrosis determined by alveolar wall thickness and collagen deposition at doses between 1 and 100 mg/kg. See FIG. 2.

Example 9

Activity in the Bleomycin Mouse Lung Damage Model (Model 2)

Male C57BU6 mice aged 8 weeks are housed on a 12 hour day/night cycle in micro-isolators cages. Food and water is allowed ad libitum. A single Bleomycin challenge (5 mU/gram) in 50 µL of saline is instilled intratracheally on day 0. Control animals receive 50 µL of saline. Groups of animals are treated with phosphotetrahydropyran test compound (Formula 1) at various doses given by osmotic pump inserted subcutaneously. Mice are studied for weight loss during the course of the experiment. At day 26 mice are sacrificed and BALF is collected for cell influx assessment in the lung airways. Total cell counts as well as phenotype are assessed. Lung histopathology including collagen deposition is assessed following standard methods. Active and total TGF-beta levels are measured in plasma obtained at day 26.

Figure 3:
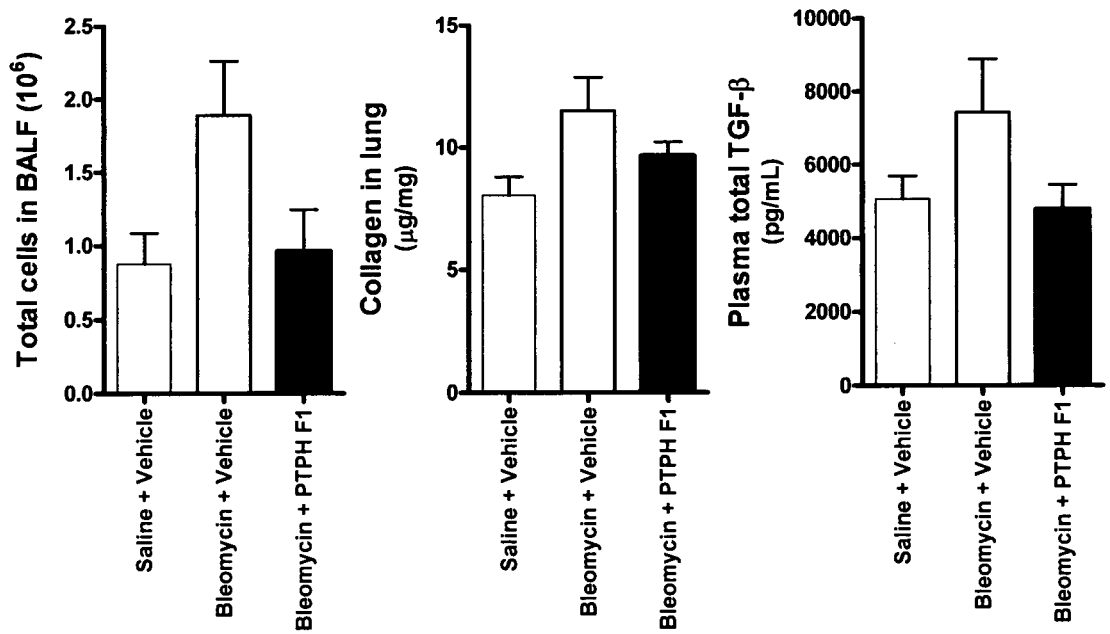
FIG. 3 illustrates that treatment with a phosphotetrahydropyran test compound effectively reduced total cell counts in BALF and decreased overall lung fibrosis determined by collagen deposition and decreased plasma TGF-beta levels at doses between 1 and 100 mg/kg.
Figure 4:
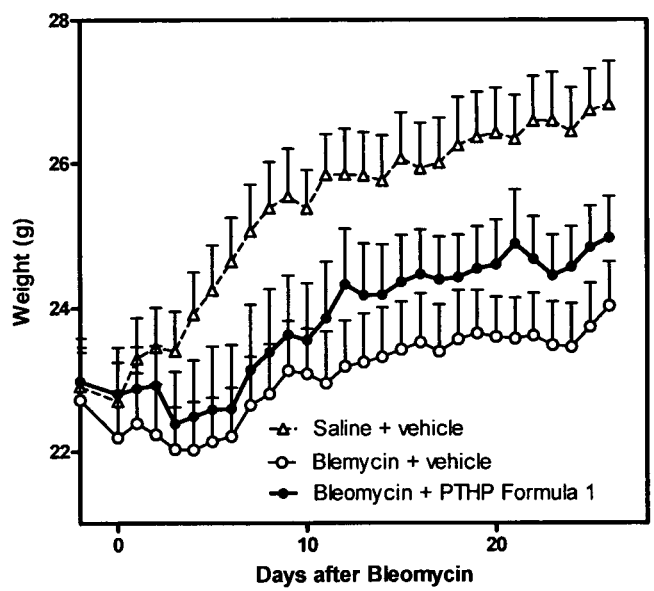
FIG. 4 illustrates that treatment with a phosphotetrahydropyran test compound effectively improved weight gain at doses between 1 and 100 mg/kg.

Treatment with phosphotetrahydropyran test compound (Formula 1) effectively improved weight gain, reduced total cell counts in BALF, decreased overall lung fibrosis determined by collagen deposition and decreased plasma TGF-beta levels at doses between 1 and 100 mg/kg. See FIGS. 3 and 4.

Example 10

Activity in the Bleomycin Mouse Lung Damage Model (Model 3)

Following the experiment described in Example 9, male C57BU6 mice aged 8 weeks are housed on a 12 hour day/night cycle in micro-isolators cages. Food and water is allowed ad libitum. A single Bleomycin challenge (5 mU/gram) in 50 µL of saline is instilled intratracheally on day 0. Control animals receive 50 µL of saline. Groups of animals are treated with various concentrations of the phosphotetrahydropyran test compound (Formula 1) dissolved in a suitable vehicle, such as PBS, by direct intratracheal administration to the lung daily for 26 days. At day 26 mice are sacrificed and BALF is collected for cell influx assessment in the lung airways. Total cell counts as well as phenotype are assessed. Lung histopathology including collagen deposition is assessed following standard methods. Active and total TGF-beta levels are measured in plasma obtained at day 26. Treatment with phosphotetrahydropyran test compound (Formula 1) effectively improved weight gain, reduced total cell counts in BALF, decreased overall lung fibrosis determined by collagen deposition and decreased plasma TGF-beta levels at doses between 1 and 100 mg/kg.

Example 11

Combination Therapy in the Bleomycin Mouse Lung Damage Model

Following the procedures described in Example 8, 9 or 10, but treating mice with a combination of the phosphotetrahydropyran test compound (Formula 1) and one compound selected from N-acetyl cysteine, aminoguanidine, anti-VEGF antibody, Batimastat, Bosentan, dexamethasone, difluoromethylornithine, Etanercept, Gefitinib, Imatinib, methylprednisolone, Pentoxifylline, Pirfenidone, prednisolone, Rosiglitazone, TGF-beta antibody, TNF-alpha antibody, and Vinblastine, lower doses of both compounds were required to achieve the same improvements in weight gain, reduction in total cell counts in BALF, decrease in overall lung fibrosis and plasma TGF-beta. For some combinations the effects were additive, while for others the effects were synergistic.

Example 12

Evaluation of the Phosphotetrahydropyran Test Compound in a Rabbit Model of Experimental Glaucoma Filtering Surgery New Zealand White rabbits (18) were subjected to a modified glaucoma filtering surgery in the left eye. The animals received either intraoperative PXS-25 at a concentration of 40 mg/mL (Group 1), intraoperative Mitomycin C (MMC) at a concentration of 0.4 mg/mL (Group 2), or intraoperative test compound and Mitomycin C (MMC) (Group 3).

Filtration surgery was performed on the left eye only. MMC, test compound (Formula 1) or the combination were delivered with a large sponge measuring 8×10 mm (dry size) cut from a Weck-Cel prior to cutting the flap and sclerostomy. The sponge pieces were placed between the conjunctiva and sclera over the determined filtration site for 3 minutes. The area was then thoroughly irrigated with 30 mL of physiologic saline. The animals were reviewed on the first day after surgery, and then weekly until bleb failure. The study was terminated after the 8 week. Fluorescein tracer studies was performed as follows. Sodium fluorescein was injected into the anterior chamber and the drainage pathway using a slit lamp based digital video camera system was recorded. The animals were sacrificed and tissue sections were prepared for immunohistochemically staining for signs of scarring and inflammation. Examination of the results revealed that the test compound (Formula 1) preserved the bleb as well as mitomycin, with healthy tissue surrounding the site of surgical intervention. In contrast, animals receiving mitomycin had very visible dead tissue surrounding the bleb.

Example 13

Improved Wound Repair in a Rabbit Wound Healing Model

Four female New Zealand White rabbits are used (per route of administration). Twenty four hours prior to the test the fur is removed from the dorsal area of each rabbit. The animals are anaesthetized by intravenous injection in the marginal ear vein (pentobarbitone). Immediately prior to injection, the skin is wiped with 70% isopropyl alcohol, followed by a 1% iodine solution. A full thickness square wound, approximately 1 cm side, is made using surgical scissors on two delineated sites. The cut does not go through the muscle fascia. Rabbits are singly caged.

The phosphotetrahydropyran test compound (Formula 1) is either applied directly to the wound (dermal route; 100 mM solution applied by spatula) or it is injected on each side of the wound (subcutaneous route; 100 mM solution injected subcutaneously using a 29 gauge needle). For the dermal route the rabbits are placed in rabbit holder for 4 hours daily until wound closure to avoid removal of test item. Treatment is continued until wound closure. The wound areas (width× length) are measured every other day until the wound appeared close (approximately 10 days). The animals are then sacrificed and the wounded tissues and surrounding skin are excised, attached to cardboard and fixed flat in 10% neutral buffered formalin. Histopathology examination is performed on sections stained with hematoxylin and eosin (H&E) to examine general tissue and cellular morphology.

Treatment with phosphotetrahydropyran test compound (Formula 1) reduced excessive scar formation, improving the visual quality of the scar and reduced skin fibrosis at the site of injury.

Example 14

Evaluation of Test Compound on Acute LPS-Induced Lung Inflammation in the Mouse

Age-matched germ-free male C57BI/6 mice (25.30±0.39 g; 6-7 week-old) were transiently anaesthetized with a mixture of isoflurane and oxygen. The vehicle-treated group received intravenous injection (iv) of saline 15 min prior to intra-tracheal instillation (i.t.) of lipopolysaccharide (LPS, 3 mg/kg). Another set of animals received i.v. injection of dexamethasone at 1 mg/kg or 2.5 mg/kg 1 hour prior to LPS. The phosphotetrahydropyran test compound was administered to the animals at 5, 15 and 30 mg/kg (iv) 15 min prior to LPS instillation. A separate group of mice was used as sham (saline/PBS) and was treated with i.v. injection of saline and i.t. injection of PBS (phosphate buffered saline).

Three hours after the LPS administration, animals were anaesthetized with urethane (25%, 100 mL/g body weight). A blood sample was collected by cardiac puncture (≅1 mL) and the animals were sacrificed by cervical dislocation. The trachea was cannulated and the lungs were lavaged with 2 mL of PBS containing EDTA (1 mM). The lavaged fluid was harvested by gentle injections and aspirations four times with 0.5 mL each, and centrifuged. The total cell count was determined on a fresh fluid specimen with Turk solution using a Neubauer chamber. Differential cell counts were determined using Cytospin technique. Aliquots of the bronchoalveolar lavage (BAL) supernatants were stored without further treatment at $-80°$ C.

Slices of each pulmonary lobe were immediately removed from the animal, weighed and either frozen in liquid nitrogen for myeloperoxidase (MPO) assay or placed in the oven for lung oedema evaluation. Determination of MPO activity was used as an index of leukocyte accumulation, where one unit of MPO activity was defined as that degrading 1 µmol hydrogen peroxide/min at 25° C. by the formula MPO (U/g)=Vmax/s×60/0.0113/0.5. Data were presented as MPO activity expressed as U/g wet tissue. To determine pulmonary oedema, the left pulmonary lobes were removed, weighed and dried at 60° C. for 48 h for wet to dry weight ratio measurements.

Figure 5:
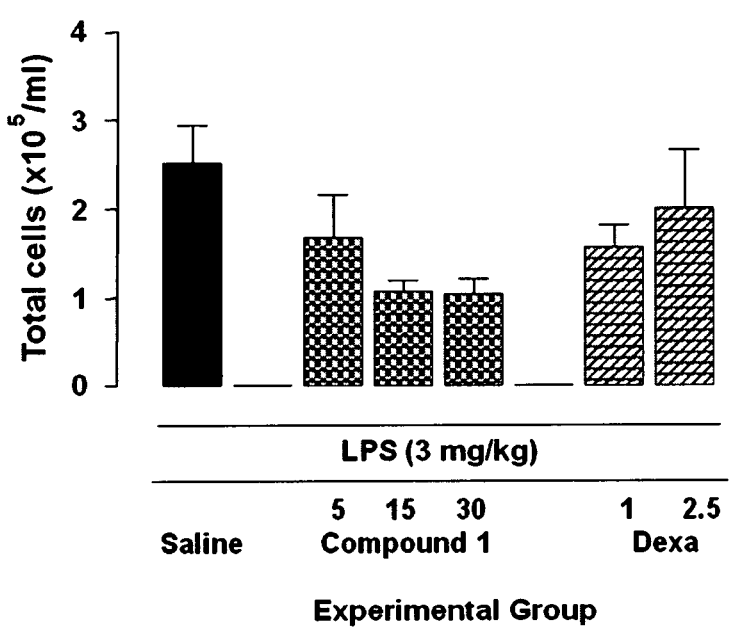
FIG. 5 illustrates that the total number of inflammatory cells recovered from the BAL fluid of LPS control group was not significantly different compared with dexamethasone and a phosphotetrahydropyran test compound (at 5 and 30 mg/kg). However, a significant inhibition of total cells was seen in the group of mice treated with phosphotetrahydropyran test compound at a dose of 15 mg/kg.

The total number of inflammatory cells recovered from the BAL fluid of LPS control group was not significantly different compared with dexamethasone and the phosphotetrahydropyran test compound (at 5 and 30 mg/kg). However, a significant inhibition of total cells was seen in the group of mice treated with phosphotetrahydropyran test compound (Formula 1; n=1 and R=2,4-dimethylphenyl) at a dose of 15 mg/kg (FIG. 5).

Figure 6:
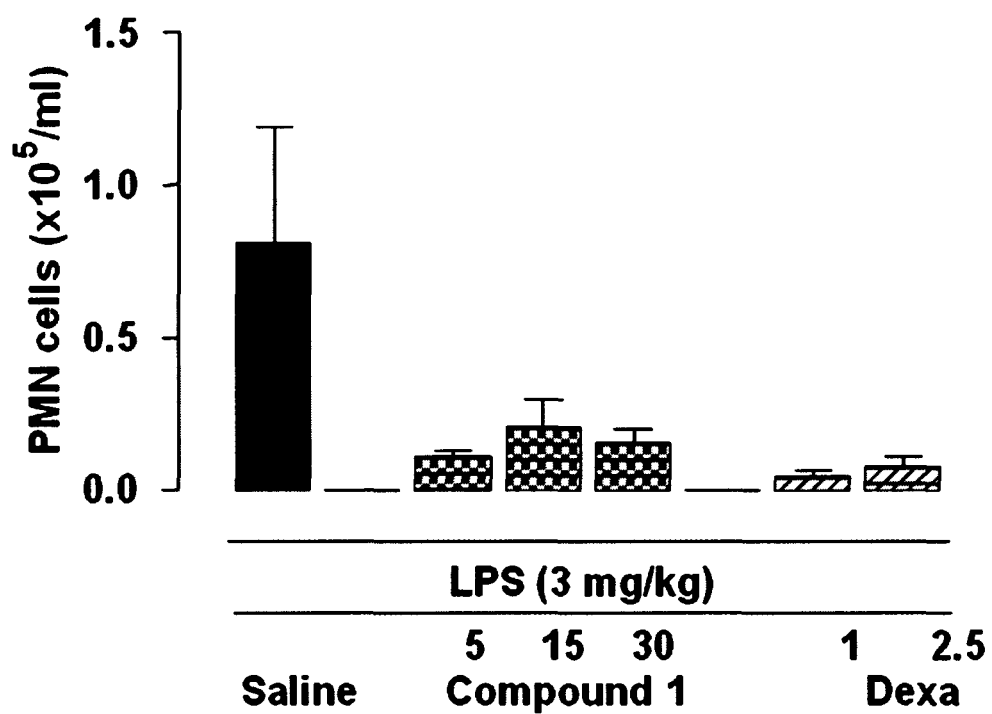
FIG. 6 illustrates that pretreatment of mice with the test compound resulted in a significant decrease of neutrophils number compared to vehicle (saline)-control group (86.7%, P<0.05). Likewise, treatment of animals with dexamethasone almost abolished the cells influx into the BAL fluid of animals with acute lung inflammation.

Approximately 30% of cells recovered from the BAL fluid of the vehicle control group were neutrophils. Pre-treatment of mice with the test compound resulted in a significant decrease of neutrophils number compared to vehicle (saline)-control group (86.7%, P<0.05). Likewise, treatment of animals with dexamethasone almost abolished the cells influx into the BAL fluid of animals with acute lung inflammation (see FIG. 6).

Example 15

Evaluation of Test Compound in a Model of Thioglycolate-Induced Peritonitis in the Mouse Germ-free male C57BI/6 mice, weighing in the target range of 21.30±0.39 g (6-7 week-old) were anaesthetised with halothane and then received by intravenous route (iv) increasing doses of the phosphotetrahydropyran test compound (5 or 15 mg/kg, −15 min), dexamethasone (1 mg/kg, −60 min) or the respective vehicle (saline 0.9%, pH 7.4). Peritoneal inflammation was induced by i.p. injection of Brewer's thioglycolate. Thioglycolate was prepared freshly (3%, w/v) in sterile saline, and 1.5 mL was injected into the intraperitoneum cavity (ip). Following 3 h treatment, animals were killed (under anesthesia) by cervical dislocation, and cells were recovered by peritoneal lavage using 5 mL of ice-cold PBS. The lavage contents were immediately stored on ice. Peritoneal exudate cells (PEC) were further diluted in 5 mL of ice-cold PBS. The total cell count was determined on a Neubauer chamber with Turk solution, whereas the differential cell counts were conducted on cytospin preparations. Peritoneal lavage was carefully confirmed to be negative for erythrocytes by microscopy to exclude the possibility that leukocyte accumulation in the peritoneal cavity was due to microbleeding, which may occur during animal preparation.

Data are expressed as Mean (±SEM) from n individual animals. Statistical analysis of data was carried out using Software Graphpad prism v4. Comparative data were analysed using ANOVA followed by Dunnett's post test and ANOVA (unpaired Student's T tests). Statistical P values less than 0.05 were taken as significant. Dose-dependent anti-inflammatory actions of the phosphotetrahydropyran test compound and dexamethasone were recorded.

Figure 7:
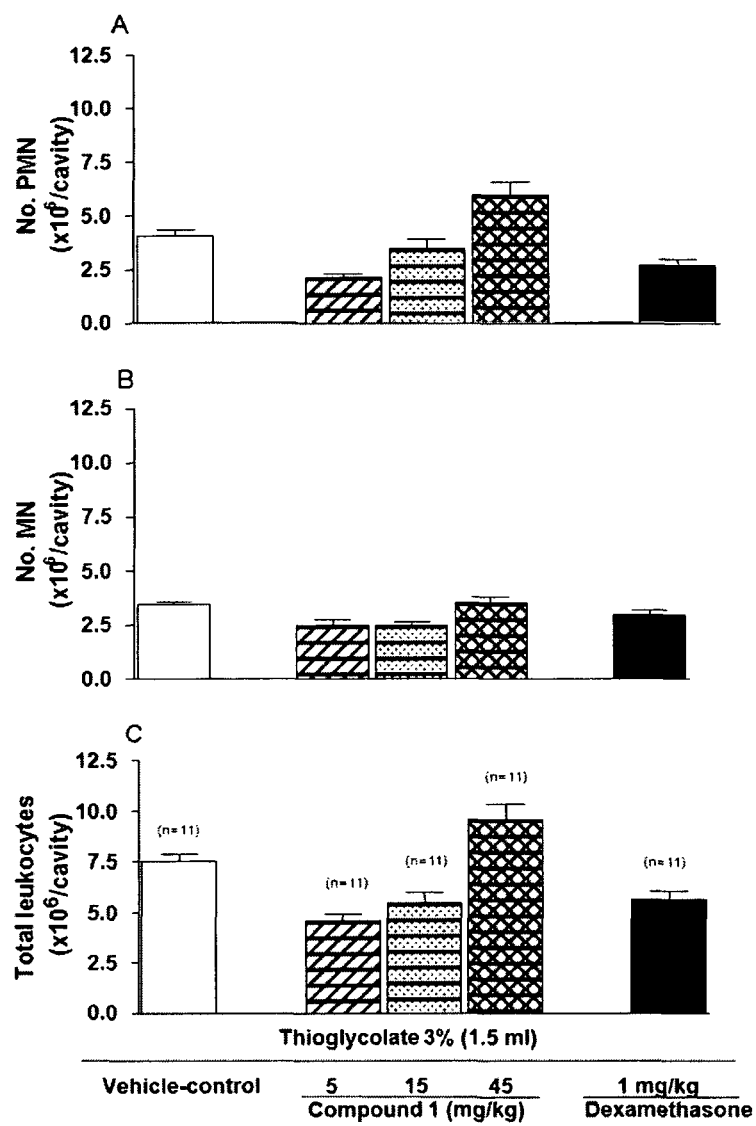
FIG. 7 shows the influence of pre-treatments with a phosphotetrahydropyran test compound and dexamethasone on thioglycolate-induced leukocyte migration in the peritoneal cavity. The results of polymorphonuclear (PMN) (A), mononuclear (MN) recruitment (B) and total cells (C) are shown as number of cells per cavity. The results are from a representative experiment with 11 mice. Significant p values for each time point are shown (Dunnett's post test and unpaired T-test).

FIG. 7 shows the influence of pre-treatments with the phosphotetrahydropyran test compound (n=1 and R=2,4-dimethylphenyl; 5-45 mg/kg, i.v., −15 min) and dexamethasone (1 mg/kg, i.v., −60 min) on thioglycolate-induced leukocyte migration in the peritoneal cavity. The results of polymorphonuclear (PMN) (A), mononuclear (MN) recruitment (B) and total cells (C) are shown as number of cells per cavity. The results are from a representative experiment with 11 mice. Significant p values for each time point are shown (Dunnett's post test and unpaired T-test).

The data summarized in FIG. 7 show the sequence of events (leukocyte influx) observed in the peritoneal cavity during the first 3 h after ip injection of thioglycolate, dexamethasone (1 mg/kg) or the test compound. In untreated C57BI/6 mice, the peritoneal total cell number was markedly higher than in mice treated with the phosphotetrahydropyran test compound (Formula 1; n=1 and R=2,4-dimethylphenyl; 5 and 15 mg/kg) and dexamethasone.

Example 16

Activity in a Bleomycin-Induced Scleroderma Animal Model

This procedure follows the methods described in Liu S, et.al. Arthritis & Rheumatism, 58, 2189-2195 (2008). 100 µL of bleomycin (0.1 units/mL in phosphate buffered saline (PBS)) or PBS is injected subcutaneously into a single location on the shaved back of C57Bl/6 mice once daily for 4 weeks. At the end of the experiments, the mice are killed by $CO_2$ administration and skin samples are collected for histologic, immunohistochemical, and hydroxyproline assays.

Quantitative analysis of biomechanical properties of skin is performed. Stiffness is determined to reflect the skin's biomechanical properties. Animals are anesthetized and their backs are shaved and depilated. A glass test chamber is mounted on the backs of the mice. This glass chamber is connected to the BTC-2000 dynamic skin analyzer which generated a vacuum and directed a laser beam to the site of interest on the skin. Skin stiffness is measured at the end of bleomycin treatment.

The phosphotetrahydropyran test compound (Formula 1) is administered (ip) at doses from 10 to 100 mg/kg for two weeks twice a day. Extra groups are treated by local administration of phosphotetrahydropyran test compound (Formula 1), given by subcutaneous injection once a day for two weeks. After the 4 week experiment, sections of skin (0.5 μm) are cut using a microtome and collected on Superfrost Plus slides. Sections are then dewaxed in xylene and rehydrated by successive immersion in descending concentrations of alcohol. Sections are stained with hematoxylin and eosin (H&E). H&E stains nuclei blue; ECM components and cytoplasm are stained in various shades of pink. The effects of the test compound (Formula 1) on inflammation are graded on a scale of 0-3: 0=no inflammatory cells, 1=few inflammatory cells, 2=moderate inflammatory cells, 3=extensive inflammatory cells. Skin from mice treated with the test compound (Formula 1) are graded 1 to 2 whereas the bleomycin treated mice that did not receive the test compound are graded as 3.

To assess the effects of the phosphotetrahydropyran test compound (Formula 1) on collagen synthesis, semiquantitative analysis using van Gieson's stain is used. Van Gieson's stain results in a deep red color for mature collagen fibers and a pink color for immature collagen fibers. Muscle and fibrin appear yellow with black nuclei. The amount of collagen fibers is reported using the following scale: 0=no collagen fibers, 1=few collagen fibers, 2=moderate amount of collagen fibers, 3=excessive amount of collagen fibers. Skin from mice treated with the test compound (Formula 1) are graded 1 to 2 whereas the bleomycin treated mice that did not receive the test compound are graded as 3.

Sections are cut and processed as described above. Immunolabeling of α-SMA is performed following the literature procedure and the effect of the test compound (Formula 1) on α-SMA expression is graded on a scale of 0-3, using the following scale: 0=no cells expressing α-SMA, 1=few cells expressing α-SMA, 2=moderate amount of cells expressing α-SMA, 3=extensive number of cells expressing α-SMA. Skin from mice treated with the test compound (Formula 1) are graded 1 to 2 whereas the bleomycin treated mice that did not receive the test compound are graded as 3.

The hydroxyproline assay is performed as a marker of collagen synthesis in wound tissues following the published procedure. Skin tissues are homogenized in saline, hydrolyzed with 2N NaOH for 30 minutes at 120° C., and hydroxyproline content is determined by modification of Neumann and Logan's reaction using chloramine T and Ehrlich's reagent, using a hydroxyproline standard curve and measuring at 550 nm. Values are expressed as μg of hydroxyproline/mg of protein. The test compound (Formula 1) significantly reduced hydroxyproline content at concentrations between 1 and 100 mg/kg-day.

Example 17

Activity in Diabetes-Induced Renal Fibrosis

C57Bl/6J mice were kept under standard animal house conditions on a normal diet. Mice were given intraperitoneal injections of STZ (Sigma, St Louis, Mo.) in sodium citrate buffer (pH 4.5) on two consecutive days (125 mg/kg/day). Blood glucose was measured by tail vein sampling using a common glucometer (Roche). Diabetes was defined as a morning blood glucose reading of >16 mM by 2 weeks after STZ. When blood glucose levels exceeded 30 mM, diabetic mice were given 0.4 U of insulin (Novo Nordisk) every second day to prevent weight loss while maintaining blood glucose levels within the hyperglycaemic range (16-30 mM). Diabetic nephropathy was evaluated in groups of 10 mice killed at four time points (2, 8, 12 and 18 weeks) after STZ. A group of normal 26-week-old mice (n=10) was used as controls.

The phosphotetrahydropyran test compound (Formula 1) is administered either (ip) at doses from 1 to 100 mg/kg twice a day for the duration of the study, or given in osmotic pumps inserted subcutaneously with stable systemic exposure of the phosphotetrahydropyran test compound (Formula 1) at levels ranging from 0.01 to 100 μM in blood.

Treatment with the phosphotetrahydropyran test compound (Formula 1) reduces glomerular hypertrophy, hypercellularity and mesangial expansion, decreases tubular dilation and atrophy and reduces interstitial expansion assessed by immunohistopathology. Fibronectin and collagen deposition in the renal parenchyma was highly reduced in phosphotetrahydropyran test compound (Formula 1) treated animals.

Example 18

Determination of the Bioavailability of Inventive Compounds in the Rat and Dog

The phosphotetrahydropyran test compound (Formula 1; n=1 and R=2,4-dimethylphenyl) was administered to rats by gavage at 10 mg/kg or intravenously at 1 mg/kg). Blood samples were taken at 15 and 30 min and at 1, 2, 3, 4, 8, 12 and 24 hours. Plasma samples were prepared by the addition of 50% acetonitrile/water (20 μL). Protein precipitation was carried out by the addition of trichloroacetic acid (20% in water, 40 μL), vortexing (20 s) and after storing at 4° C. for 60 minutes, centrifugation (10,000 rpm) in a microcentrifuge for 5 min. The supernatant was subsequently separated and 25 μL injected directly onto the column for LC-MS analysis. Analysis of the data compared to blood samples spiked with known concentrations of the test compound revealed that the bioavailability of the test compound was 7.7%.

When the study was repeated with the test compound of Formula II (X=H, Px=tert-butyl), the bioavailability was determined to be 52% when concentrations the phosphotetrahydropyran test compound (Formula 1; n=1 and R=2,4-dimethylphenyl) were quantitated in plasma.

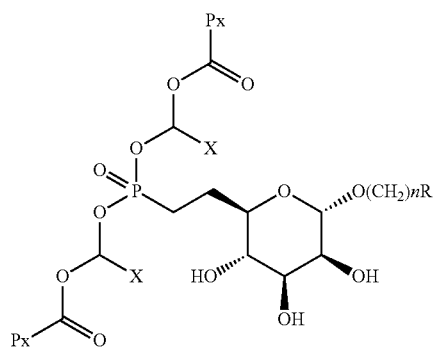

We claim:

1. A method to modulate wound healing processes in a subject, said method comprising the administration of a composition containing an effective amount of a phosphonate prodrug of a phosphonotetrahydropyran compound of a compound of Formula I, and an acceptable pharmaceutical carrier,

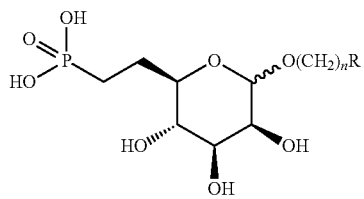

Formula I wherein the phosphonate prodrug is a mono- or di-ester of the phosphonic acid functionality; and wherein n is an integer from 0 to 3, the —O(CH$_2$)$_n$R group is in an axial or equatorial position, and R is lower alkyl, or optionally substituted heteroaryl or optionally substituted aryl wherein the substituent is selected from the group consisting of —Cl, —F, CF$_3$, CH$_3$, CH$_2$CH$_3$, —OCH$_3$, —OCF$_3$, —(CH$_2$)$_m$CO$_2$R$^1$, —(CH$_2$)$_m$OR$^2$, —(CH$_2$)$_m$CONHR$^2$, —(CH$_2$)$_m$NHR$^2$, and —(CH$_2$)$_m$CONR$^2$R$^3$, wherein m is an integer from 0 to 3; R$^1$ is selected from the group of consisting of H, alkyl and aryl; and R$^2$ and R$^3$ are independently selected from the group consisting of H, alkyl, aryl and acyl.

2. The method of claim 1 where the subject has a disease or disorder associated with the deposition of excess collagen, fibronectin and or other extracellular matrix components.

3. The method of claim 2 where the disease or disorder is lung fibrosis, glaucoma, scleroderma, liver fibrosis, cardiac fibrosis, renal fibrosis or renal failure.

4. The method of claim 1 where wound healing process is subsequent to a surgical procedure.

5. The method of claim 4 where the surgical procedure involves eye surgery, is performed on internal organs and tissues, is performed on the epidermal layer or is a procedure to repair tendon injury.

6. The method of claim 5 where the surgical procedure is performed on the epidermal layer and may lead to keloid formation or is associated with cosmetic or plastic surgery.

7. The method of claim 1 where the composition is administered to the site of inflammation and wound healing.

8. The method of claim 7 where the composition is administered directly to the lung, or to the eye.

9. A method of treating pulmonary fibrosis, comprising administering to a subject in need of treatment, an effective amount of a composition comprising a phosphonate prodrug of a phosphonotetrahydropyran compound of Formula I:

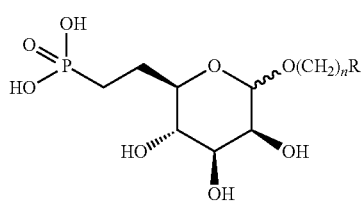

Formula I wherein the phosphonate prodrug is a mono- or di-ester of the phosphonic acid functionality; and wherein n is an integer from 0 to 3, the —O(CH$_2$)$_n$R group is in an axial or equatorial position, and R is lower alkyl, or optionally substituted heteroaryl or optionally substituted aryl wherein the substituent is selected from the group consisting of —Cl, —F, CF$_3$, CH$_3$, CH$_2$CH$_3$, —OCH$_3$, —OCF$_3$, —(CH$_2$)$_m$CO$_2$R$^1$, —(CH$_2$)$_m$OR$^2$, —(CH$_2$)$_m$CONHR$^2$, —(CH$_2$)$_m$NHR$^2$, and —(CH$_2$)$_m$CONR$^2$R$^3$, wherein m is an integer from 0 to 3; R$^1$ is selected from the group of consisting of H, alkyl and aryl; and R$^2$ and R$^3$ are independently selected from the group consisting of H, alkyl, aryl and acyl.

10. The method of claim 9, wherein the subject suffers from idiopathic pulmonary fibrosis or other fibrotic disorders of the lung.

11. The method of claim 9 wherein the phosphonate prodrug is co-administered with a compound selected from the group consisting of N-acetyl cysteine, aminoguanidine, anti-VEGF antibody, Batimastat, Bosentan, dexamethasone, difluoromethylornithine, Etanercept, Gefitinib, Imatinib, methylprednisolone, Pentoxifylline, Pirfenidone, prednisolone, Rosiglitazone, TGF-beta antibody, TNF-alpha antibody, and Vinblastine.

12. The method of claim 1 wherein the phosphonate prodrug is selected from the group consisting of:

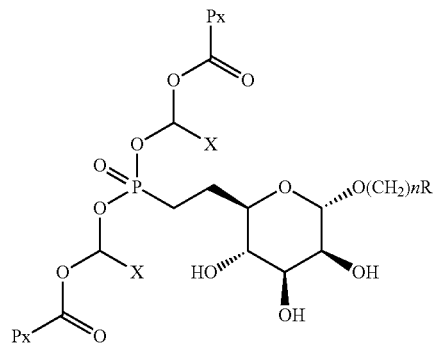

and

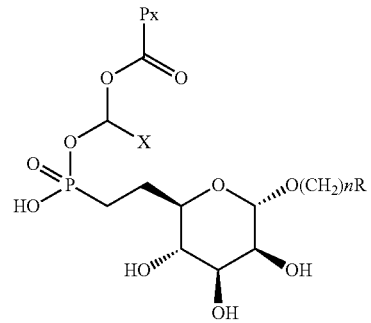

wherein X is a hydrogen or substituted alkyl and Px is alkyl.

13. The method of claim 1 wherein the subject is a human.

14. A pharmaceutical composition for modulating wound healing processes or treating pulmonary fibrosis in a subject, comprising a phosphonate prodrug of a phosphonotetrahydropyran compound of a compound of Formula I:

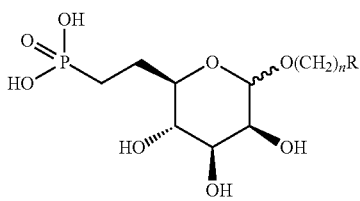

Formula I and an acceptable pharmaceutical carrier wherein the phosphonate prodrug is a mono- or di-ester of the phosphonic acid functionality; and wherein n is an integer from 0 to 3, the —O(CH$_2$)$_n$R group is in an axial or equatorial position, and R is lower alkyl, or optionally substituted heteroaryl or optionally substituted aryl wherein the substituent is selected from the group consisting of —Cl, —F, CF$_3$, CH$_3$, CH$_2$CH$_3$, —OCH$_3$, —OCF$_3$, —(CH$_2$)$_m$CO$_2$R$^1$, —(CH$_2$)$_m$OR$^2$, —(CH$_2$)$_m$CONHR$^2$, —(CH$_2$)$_m$NHR$^2$, and —(CH$_2$)$_m$CONR$^2$R$^3$, wherein m is an integer from 0 to 3; R$^1$ is selected from the group of consisting of H, alkyl and aryl; and R$^2$ and R$^3$ are independently selected from the group consisting of H, alkyl, aryl and acyl.

15. The pharmaceutical composition of claim 14 wherein the phosphonate prodrug is selected from the group consisting of:

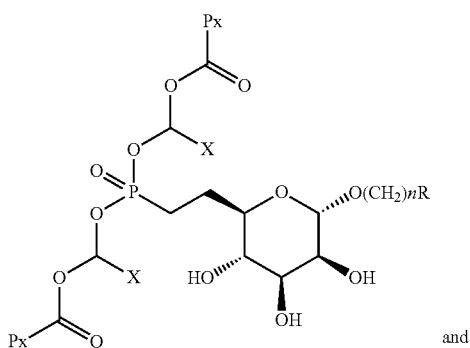

and

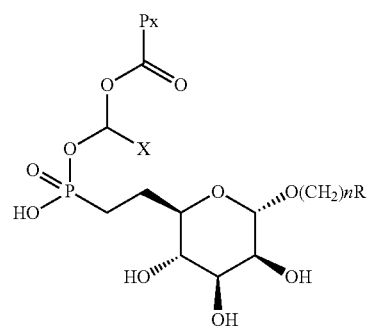

wherein X is a hydrogen or substituted alkyl and Px is alkyl.

16. The pharmaceutical composition of claim 15 wherein phosphonate prodrug is selected from the group consisting of:

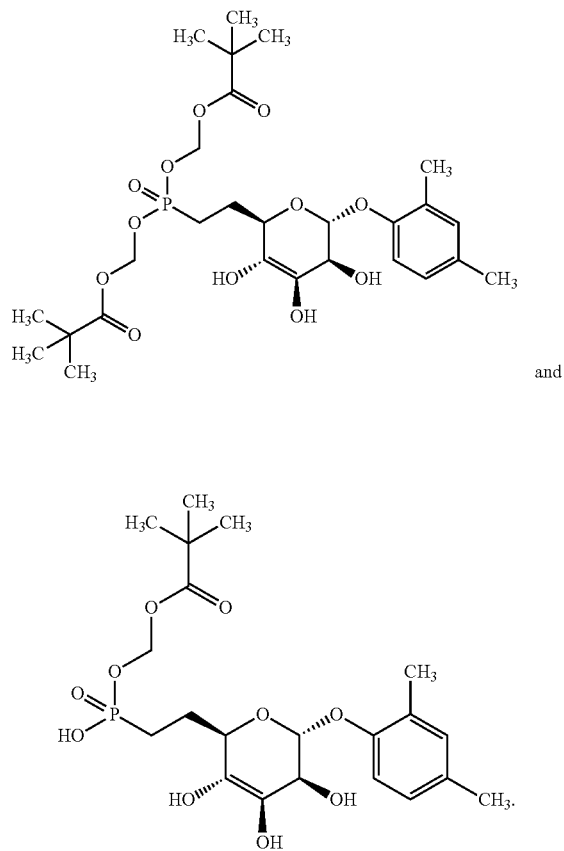

17. The pharmaceutical composition of claim 14, wherein the composition is for treating pulmonary fibrosis and further comprises a compound selected from the group consisting of N-acetyl cysteine, aminoguanidine, anti-VEGF antibody, Batimastat, Bosentan, dexamethasone, difluoromethylornithine, Etanercept, Gefitinib, Imatinib, methylprednisolone, Pentoxifylline, Pirfenidone, prednisolone, Rosiglitazone, TGF-beta antibody, TNF-alpha antibody, and Vinblastine.

18. The method of claim 12 wherein phosphonate prodrug is selected from the group consisting of:

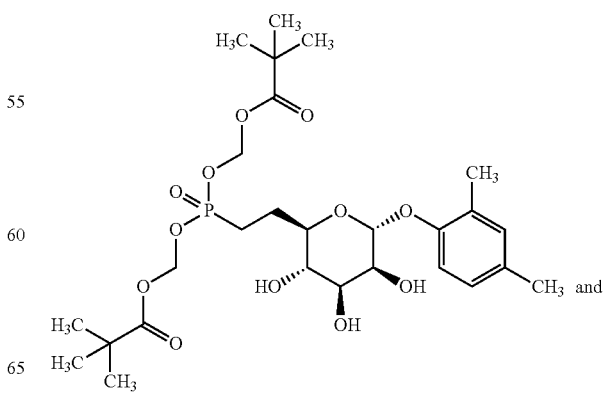

and

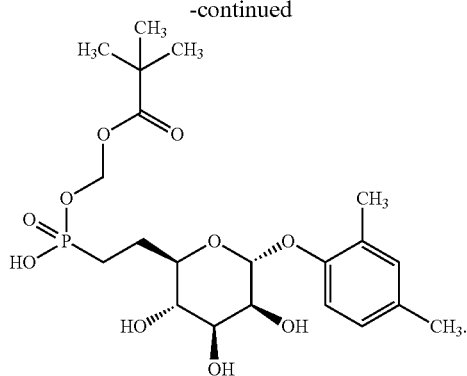
19. The method of claim 9 wherein the prodrug is selected from the group consisting of:
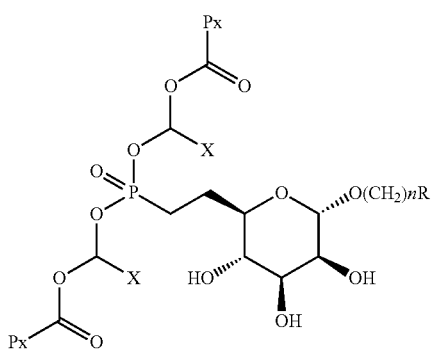
and
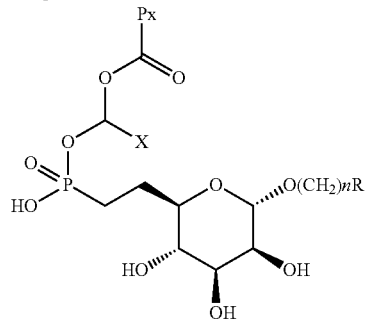
wherein X is a hydrogen or substituted alkyl and Px is alkyl.
20. The method of claim 19 wherein the phosphonate prodrug is selected from the group consisting of:
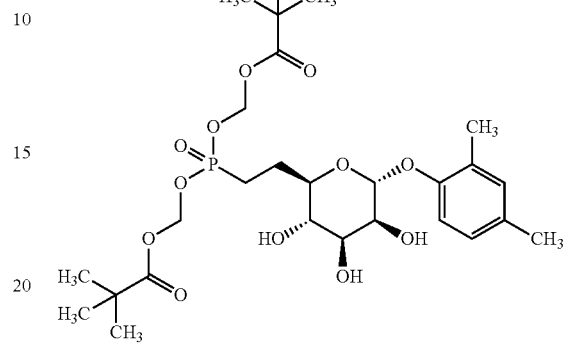
and
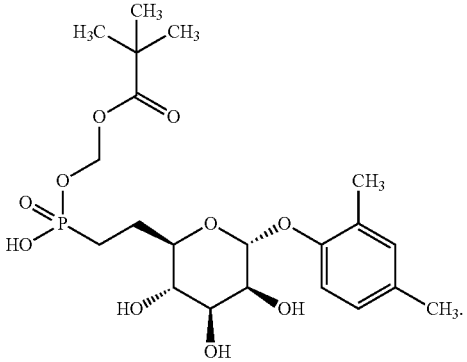
* * * * *